United States Patent
Suter et al.

(10) Patent No.: US 8,770,974 B2
(45) Date of Patent: Jul. 8, 2014

(54) SET OF DENTAL DRILLS

(75) Inventors: Edmund Suter, Niederdorf (CH); Steffen Kühne, Moehlin (CH); Patrick Streff, Weil am Rhein (DE)

(73) Assignee: Straumann Holding AG, Basel (CH)

(*) Notice: Subject to any disclaimer, the term of this patent is extended or adjusted under 35 U.S.C. 154(b) by 447 days.

(21) Appl. No.: 12/637,000

(22) Filed: Dec. 14, 2009

(65) Prior Publication Data

US 2010/0151412 A1    Jun. 17, 2010

(30) Foreign Application Priority Data

Dec. 15, 2008 (CH) ...................................... 2032/08

(51) Int. Cl.
*A61C 3/02* (2006.01)
*A61C 8/00* (2006.01)

(52) U.S. Cl.
CPC ........ *A61C 8/0089* (2013.01); *A61C 3/02* (2013.01)
USPC ............................................. 433/165; 433/75

(58) Field of Classification Search
USPC ............... 433/165–166, 197–198, 72, 74–76; 606/96
See application file for complete search history.

(56) References Cited

U.S. PATENT DOCUMENTS

| | | | |
|---|---|---|---|
| 4,580,979 A | | 4/1986 | Leonhard |
| 5,320,529 A | * | 6/1994 | Pompa ............................ 433/76 |
| 5,816,807 A | * | 10/1998 | Matsutani et al. ............ 433/165 |
| 6,863,529 B2 | * | 3/2005 | Strong et al. .................. 433/165 |
| 7,402,040 B2 | * | 7/2008 | Turri .............................. 433/165 |
| 2005/0170311 A1 | * | 8/2005 | Tardieu et al. .................. 433/76 |
| 2006/0093988 A1 | * | 5/2006 | Swaelens et al. ............... 433/76 |
| 2006/0121410 A1 | | 6/2006 | Aravena |
| 2006/0210949 A1 | * | 9/2006 | Stoop ............................ 433/165 |
| 2007/0099150 A1 | * | 5/2007 | Muller et al. ................. 433/165 |
| 2008/0220390 A1 | | 9/2008 | Klein |
| 2010/0015573 A1 | | 1/2010 | Holzner et al. |

FOREIGN PATENT DOCUMENTS

| | | |
|---|---|---|
| CH | 681854 A5 | 3/1990 |
| DE | 3446026 A1 | 12/1983 |
| EP | 0 281 813 A1 | 2/1988 |
| WO | WO 99/26540 | 6/1999 |
| WO | WO 01/49201 A1 | 7/2001 |
| WO | WO 02/24083 A2 | 3/2002 |
| WO | WO 03/071972 A1 | 9/2003 |
| WO | WO 2006/130067 A1 | 12/2006 |
| WO | WO 2007/067105 A1 | 6/2007 |
| WO | WO 2008/089885 A1 | 7/2008 |

* cited by examiner

*Primary Examiner* — Hao D Mai

(74) *Attorney, Agent, or Firm* — Novak Druce Connelly Bove + Quigg LLP

(57) ABSTRACT

Set of dental drills having two or more dental drills (10, 10'), each of dental drills (10, 10') having a cutting portion (20, 20') that has an end-face drilling end (22, 22') and a shank portion (30, 30') that has a receiving region (32, 32') intended to be received in a drill holding device. The shank portions (30, 30') of the dental drills each have a substantially circular-cylindrical guide region (40, 40') for guiding the dental drills, the guide regions (40, 40') of the two or more dental drills being of the same diameter.

14 Claims, 2 Drawing Sheets

SET OF DENTAL DRILLS

FIELD OF THE INVENTION

The present invention relates to a set of dental drills.

BACKGROUND

Known in dental implantology, for the preparation of an implant bed, is the practice of using a set of a plurality of differing dental drills, which set comprises, for example, a milling cutter, a pilot drill, a profile drill, a spiral drill (also twist drill) and a threading tap drill.

Broadly, the procedure in the preparation of an implant bed is as follows: Firstly, the bone surface is exposed, and smoothed by means of a milling cutter. The implantation site is marked by means of the milling cutter, and possibly widened, in which latter case a plurality of milling cutters of increasing diameters are used. The implant bed is then prepared by means of appropriate pilot drills, in order to determine the drilling axis. The drilled hole is widened to the required size by means of spiral drills. A profile drill is used to match the profile of the drilled hole to the shape of the provided implant. In a terminal step, an internal thread is then realized in the drilled hole by means of a threading tap drill.

In order to ensure an optimum implantation axis, a drilling template is usually used for the preparation of the implant bed. Such drilling templates serve to guide dental drills and to prevent slipping or deviation errors during the drilling process. A drilling template is designed in such a way that it can be used for the preparation of one or more implantation sites. It has one or more drilling holes, into which the dental drills are inserted prior to drilling. Frequently, standardized metal drill sleeves are inserted into the drilling holes of the drilling template, for example by being polymerized or pressed in, in order further to increase the precision of the drilling. Such a method is disclosed, for example, in WO 99/26540.

In the course of the drilling process, it is usually necessary for the drilling holes or drill sleeves in the drilling template to be matched, through use of corresponding reduction sleeves, to the diameter of the dental drill being used at a given time. Alternatively, appropriate drilling spoons (also drill handles) can be inserted into the drilling holes or drill sleeves. Thus, an entire set of differing reduction sleeves or drilling spoons is required for the complete preparation of a single implant bed. Because the reduction sleeves or drilling spoons must be exchanged continually, this results in increased complexity and potential for error.

Moreover, in the case of individual dental drills, particularly in the case of profile drills, it can be the case that these drills are too broad for a reduction sleeve or drilling spoon. In this case, the drilling has to be performed without guidance, and the risk of a drilling inaccuracy is significantly greater.

SUMMARY OF THE INVENTION

A drill set is provided in accordance with various embodiments of the present invention to simplify the guidance of dental drills during the entire drilling process, and which is particularly useful for guidance of broad dental drills.

According to one embodiment, a set of dental drills comprises two or more dental drills. Each of the dental drills includes a cutting portion that has a frontal drilling end and a shank portion that has a receiving end region intended to be received in a drill holding device. The shank portion has a substantially circular-cylindrical guide region for guiding the dental drill, and the guide regions of the two or more dental drills are of the same diameter.

Because the guide regions of the dental drills are of identical diameter, it is not necessary to change the reduction sleeve or the drilling spoon during the drilling process. The diameter of the guide region of the individual dental drills, and therefore the necessary inner diameter of the drill guide, is thus non-dependent on the diameter of the cutting portion of the dental drills. Since it is no longer necessary for the reduction sleeves to be changed during drilling, the drilling process is simplified.

In one embodiment, the guide regions of all dental drills of the set of dental drills are, additionally, of the same height. The height of the guide region has a determinant effect upon the maximum drilling depth that can be achieved with the corresponding dental drill. For this reason, it is advantageous if all dental drills of a set have a guide region of identical height, such that there is no risk of confusion in this regard.

Preferably, the guide region of each dental drill has a diameter of 2.6 to 3.0 mm, particularly of 2.8 mm. The length of the guide region of the dental drill is preferably about 2 to 10 mm, particularly about 4 to 6 mm. The guide region is thereby optimally matched to commercially available drill guides.

In one embodiment, the shank portion of the dental drill has a drilling stop. Optionally the shank portion has a groove or a bead for the purpose of fastening a drilling stop. The integration of a drilling stop, groove or bead for the purpose of fastening a separate drilling stop guarantees that a certain maximum drilling depth cannot be exceeded during drilling. Such a drilling stop projects radially beyond the shank of the dental drill, and bears on the drill sleeve or reduction sleeve as soon as the required maximum drilling depth is attained. Further lowering of the dental drill into the drilled hole is then not possible.

In one embodiment, the shank portion of the dental drill additionally has an insertion region, for the lateral insertion of the dental drill into a drill guide. This insertion region is preferably designed to be narrower than the guide region. Depending on the width of the cutting portion of the dental drill, the insertion region is moreover preferably even narrower than the cutting portion of the dental drill. To enable the dental drills to be inserted laterally into a drill guide, this drill guide must have a lateral slot that is at least as broad as the insertion region of each dental drill. The provision of an insertion region on the dental drill makes it possible for even those drills having a particularly thick cutting portion, and particularly profile drills, to be inserted into a drill guide. As a result, optimum compliance with the required implantation axis can be ensured, even in the case of dental drills whose cutting portion is of a greater diameter than the inner diameter of the drill guide.

Preferably, the insertion region has a diameter of 1.2 to 2.2 mm, particularly of 1.7 mm. An insertion region having this diameter is sufficiently "thick", and therefore sufficiently stable, to prevent the drill from breaking off under the usual stresses of the drilling process. On the other hand, however, the insertion region should be significantly narrower than the guide region, such that precise guidance of the drill is ensured, even in the case of a drill guide having a lateral slot, which, clearly, must be matched to the diameter of the insertion region. Drills whose guide region has a diameter of about 2.8 mm and whose insertion region has a diameter of about 1.7 mm fulfill these requirements in an optimal manner.

In one embodiment, the set of dental drills comprises at least one profile drill. In a further embodiment, the set of dental drills comprises at least one threading tap drill. The above-mentioned advantages of the set are most particularly evident in the case of profile drills and threading tap drills, which have a relatively broad cutting portion.

In a further embodiment, the set comprises at least one milling cutter, pilot drill, profile drill, spiral drill (also known as twist drill) and threading tap drill. Such a set enables the dental surgeon to perform the entire preparation of the implantation bed with the use of one set. Moreover, the same drill guide can be used for all drill types.

In a further embodiment, not all cutting portions of the dental drills are of the same diameter. Such a set with dental drills of differing diameters enables the progressive widening of the drilled hole to be performed with the use of a single set. Moreover, the same drill guide can be used for all dental drills of the set. Preferably, the various dental drills of the set are marked according to the diameter of their cutting portion, for example by a color marking. Such a (color) marking can be applied, for example, to the shank portion of the dental drills. Preferably, the set comprises dental drills whose cutting portions have a diameter of 3.3 mm, of 4.1 mm or of 4.8 mm.

According to another embodiment, a dental implantology set is provided that comprises a set of dental drills and a drill guide. The term "drill guide" means one or more of drill sleeves, reduction sleeves, drilling spoons and similar aids for the purpose of guiding the dental drill. In this case, the diameter of the guide region of the dental drills corresponds to the inner diameter of the drill guide. The drill guide is thus matched to the dental drills that are likewise included in the dental implantology set.

In one embodiment, the dental implantology set additionally has a drilling stop. The combination of the set of dental drills with a drill guide and a drilling stop enables the preparation of the implant bed to be realized in an optimal manner. The drill guide allows control of the optimum implantation axis, while the drilling stop prevents excessively deep penetration into the jaw bone.

DETAILED DESCRIPTION

Figure 1:
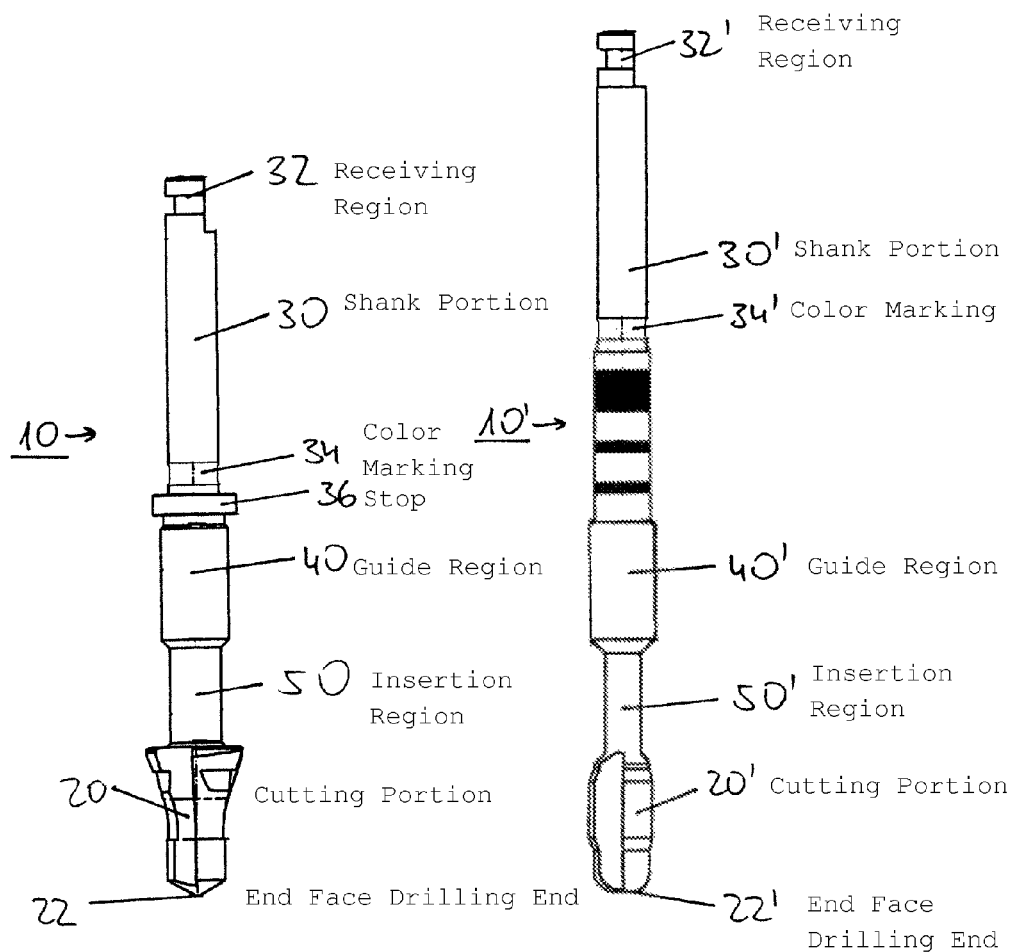
FIG. 1 is a side plan view of a set of dental drills according to one embodiment of the invention.

FIG. 1 shows a set of two dental drills 10, 10', consisting of a profile drill 10 and a threading tap drill 10'. Each of the dental drills 10, 10' has a cutting portion 20, 20' and a shank portion 30, 30'. An end-face drilling end 22, 22' is provided at the lower end of the cutting portion 20, 20'. At the upper end of the shank portion 30, 30' there is a receiving region 32, 32', which is intended to be received in a drill holding device. The shank portions 30, 30' moreover have a substantially circular-cylindrical guide region 40, 40' for guiding the dental drill 10, 10' during the drilling process. The guide regions 40, 40' of the two dental drills 10, 10' are of the same diameter. The shank portions 30, 30' additionally have an insertion region 50, 50', which enables the dental drills to be inserted laterally into a drill guide. The diameter of the respective cutting portion 20, 20' is coded by a color marking 34, 34' on the shank portions 30, 30' of the dental drills 10, 10'. The profile drill 10 moreover has a drilling stop 36, which defines a maximum drilling depth.

Figure 2:
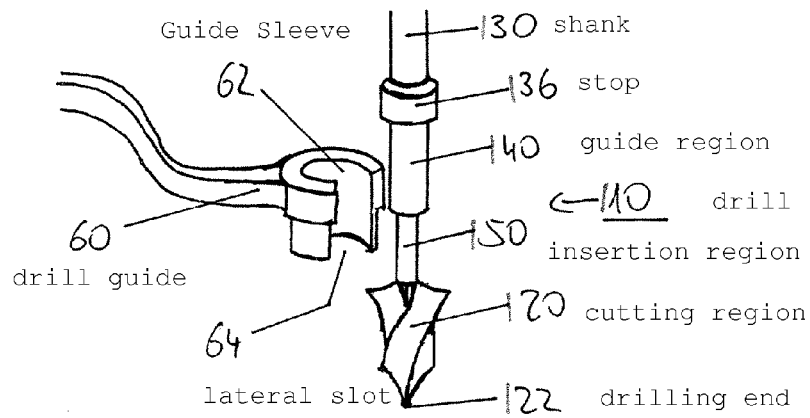
FIG. 2 is a side perspective view of a schematic representation of a dental drill from a set according to one embodiment of the invention, the set including a drill guide.

FIG. 2 shows schematically how a dental drill 110 from a set according to one embodiment of the invention is inserted laterally into a drill guide 60. For this purpose, the insertion region 150 of the dental drill 110 is guided through a lateral slot 64 in the guide sleeve 62 of the drill guide 60. Subsequent lowering of the dental drill 110 in the drill guide 60 brings the guide region 140 of the dental drill to the level of the guide sleeve 62. When, during drilling, the drilling stop 136 of the dental drill 110 meets the upper edge of the guide sleeve 62, the required drilling depth has been attained and the dental drill 110 cannot be lowered further.

Figure 3:
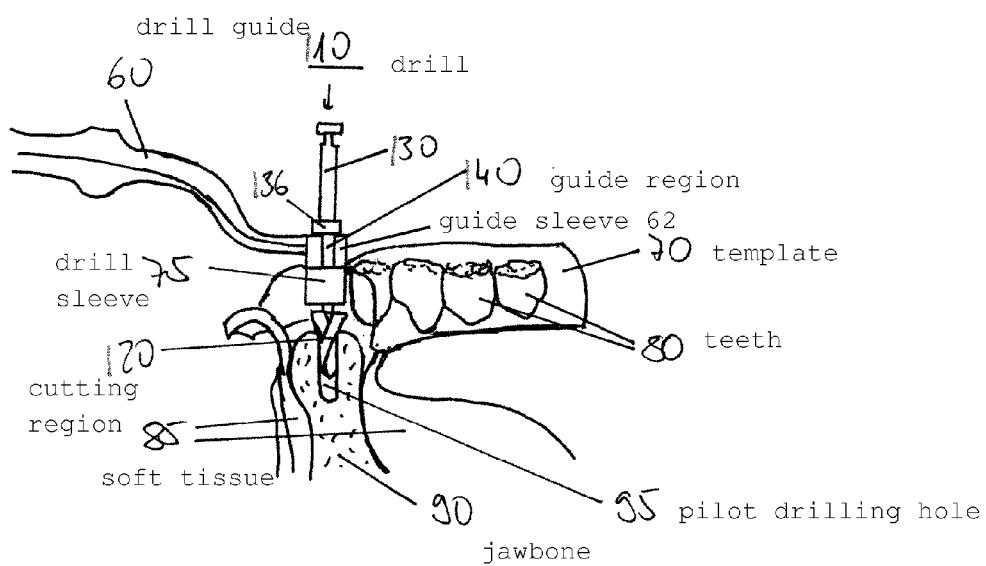
FIG. 3 is a side perspective view of a schematic representation of the drilling process using a dental drill from a set according to one embodiment of the invention, in combination with a drilling template.

FIG. 3 shows a schematic representation of a drilling template 70 that is applied to the dentition 80 of a patient. The drilling template 70 has, at the prepared implantation site, a drilling hole, in which a drill sleeve 75 is fastened. Around the implantation site, the soft tissue 85 is folded back, and the jaw bone 90, in which a pilot drilling 95 has already been made, is exposed. For the further preparation of the implant bed in the jaw bone 90, a dental drill 110 according to one embodiment of the invention has been inserted into the drill guide 60 and lowered into the drill sleeve 75. As a result, the dental drill 110 is guided in the guide region 140 during the drilling process, and slipping or deviation errors are prevented. The drilling stop 136 ensures that the required maximum drilling depth is not exceeded. Subsequently, progressively wider dental drills from a set of such dental drills are inserted into the drill guide 60 and the drill sleeve 75, and the implantation bed is widened to the required size.

The invention claimed is:

1. A set of dental drills comprising:
   two or more dental drills, and a drill guide having an inner diameter and a lateral slot, each of the dental drills comprising
      a cutting portion that has an end-face drilling end at one end of the dental drill, and
      a shank portion that has
         a receiving region at an opposing end of the dental drill, the receiving region configured to be received in a drill holding device,
         a substantially circular-cylindrical guide region having a diameter that is matched to the inner diameter of the drill guide; the guide region configured to guide the dental drill within the matching inner diameter of the drill guide during a drilling process, and
         an insertion region configured to laterally insert the dental drill into the lateral slot of the drill guide and secure the guide region of the dental drill within the inner diameter of the drill guide, wherein the lateral slot of the drill guide is at least as broad as the insertion region; and wherein
      the guide region has a wider diameter than the receiving region and the insertion region,
      the guide regions of the two or more dental drills have the same diameter, and
      a maximum diameter of the insertion region is smaller than a maximum diameter of the guide region and a maximum diameter of the cutting portion of the dental drill.

2. The set of dental drills as claimed in claim 1, wherein the guide regions of all the dental drills are of the same height.

3. The set of dental drills as claimed in claim 1, wherein the guide region of each dental drill has a diameter of 2.6 to 3.0 mm.

4. The set of dental drills as claimed in claim 1, wherein the guide region of each dental drill has a diameter of 2.8 mm.

5. The set of dental drills as claimed in claim 1, wherein the guide region of each dental drill has a length of about 4 to 6 mm.

6. The set of dental drills as claimed in claim 1, wherein the shank portion of each dental drill has a drilling stop between the receiving region and guide region configured to define a maximum drilling depth and having a greater diameter than the guide region.

7. The set of dental drills as claimed in claim 1, wherein the shank portion of each dental drill has a groove or a bead for fastening a drilling stop.

8. The set of dental drills as claimed in claim 1, wherein the insertion region has a diameter of 1.2 to 2.2 mm.

9. The set of dental drills as claimed in claim 1, wherein the insertion region has a diameter of 1.7 mm.

10. The set of dental drills as claimed in claim 1, wherein the set comprises at least one profile drill.

11. The set of dental drills as claimed in claim 1, wherein the set comprises at least one threading tap drill.

12. The set of dental drills as claimed in claim 1, wherein the set comprises at least one milling cutter, pilot drill, profile drill, spiral drill and threading tap drill.

13. The set of dental drills as claimed in claim 1, wherein not all cutting portions of the dental drills are of the same diameter.

14. The set of dental drills as claimed in claim 1, further comprises a drilling stop.

* * * * *